United States Patent [19]

Goldberg et al.

[11] Patent Number: 5,085,629

[45] Date of Patent: Feb. 4, 1992

[54] BIODEGRADABLE STENT

[75] Inventors: Jay Goldberg, Northbrook, Ill.; Richard Sinclair, Columbus, Ohio

[73] Assignee: Medical Engineering Corporation, Del.

[21] Appl. No.: 414,651

[22] Filed: Sep. 27, 1989

Related U.S. Application Data

[63] Continuation-in-part of Ser. No. 254,547, Oct. 6, 1988, abandoned.

[51] Int. Cl.⁵ .......................... A61M 5/00; A61F 2/04
[52] U.S. Cl. ........................................ 604/8; 623/12; 606/154; 128/898; 604/281
[58] Field of Search ................. 604/8, 264, 265, 275; 128/656-658, 898; 623/12; 606/151, 154, 228, 230

[56] References Cited

U.S. PATENT DOCUMENTS

| | | | |
|---|---|---|---|
| 4,045,418 | 8/1977 | Sinclair | 528/357 |
| 4,212,304 | 7/1980 | Finney | 604/170 |
| 4,300,565 | 11/1981 | Rosencraft et al. | 128/335.5 |
| 4,379,138 | 4/1983 | Pitt et al. | 424/8 |
| 4,531,933 | 7/1985 | Norton et al. | 604/8 |
| 4,605,730 | 8/1986 | Shalaby et al. | 528/357 |
| 4,610,657 | 9/1986 | Bensow | 604/8 |
| 4,650,488 | 3/1987 | Bay et al. | 623/12 |
| 4,674,506 | 6/1987 | Alcond | 128/334 R |
| 4,700,704 | 10/1987 | Jamiolkowski et al. | 128/335.5 |
| 4,791,929 | 12/1988 | Jarrett et al. | 128/375.5 |
| 4,826,945 | 5/1989 | Cohn et al. | 528/76 |
| 4,863,472 | 9/1989 | Tormala et al. | 623/16 |
| 4,874,360 | 10/1989 | Goldberg et al. | 604/8 |
| 4,916,193 | 4/1990 | Tang et al. | 525/413 |
| 4,994,074 | 2/1991 | Bezwada et al | 606/230 |

OTHER PUBLICATIONS

Bergman et al, Investigative Urology, vol. 16, No. 1, pp. 48–49 (Jul. 1978).
Assimos et al, Urological Research, vol. 12, pp. 291–293 (1984).
Barrows, Clinical Materials, vol. 1, pp. 233–257 (1986).
Flam et al, Investigative Urology, vol. 33, No. 6, pp. 490–494 (Jun. 1989).

*Primary Examiner*—C. Fred Rosenbaum
*Assistant Examiner*—Mark O. Polutta
*Attorney, Agent, or Firm*—Stuart E. Krieger

[57] ABSTRACT

A biodegradable, biocompatible, resorbable infusion stent comprising a terpolymer of:
 (a) L(−)lactide,
 (b) glycolide, and
 (c) epsilon-caprolactone.

This invention includes a method for treating ureteral obstructions or impairments by utilizing a biodegradable, biocompatible, resorbable infusion stent, and a method for controlling the speed of resorption of the stent.

32 Claims, No Drawings

BIODEGRADABLE STENT

This is a continuation-in-part of application Ser. No. 254,547 filed on Oct. 6, 1988, and now abandoned.

BACKGROUND OF THE INVENTION

1. Field of the Invention

This invention relates to the preparation of ureteral stents from biodegradable polymers of lactic acid.

2. Description of the Prior Art

Ureteral stents are often used to maintain fluid drainage from the renal pelvis to the bladder when the ureter is obstructed or otherwise impaired, and also for providing support to a collapsed or restricted ureter.

Very often, ureteral stents are positioned in a patient on a temporary basis to provide drainage from the kidney to the bladder following surgery. The stent is generally coiled or looped at opposite ends to prevent upward or downward migration from a predetermined position in the ureter caused by peristaltic action or other body motion that would impose forces on the stent to move it from its predetermined position.

Certain ureteral stents have the capability of infusing fluids into the kidney and are commonly referred to as "infusion stents".

In many situations where the ureteral stent is installed for short term usage, an additional surgical procedure must be employed to remove the stent after its purpose has been fulfilled.

A ureteral stent that is made of a biodegradable and biocompatible material would assure its safe and innocuous disappearance without the need for a second surgical procedure for its removal after it has completed its function.

Canadian Patent No. 808,731 to Fouty discloses the preparation of high molecular weight polylactides with an anionic coordination catalyst containing a divalent metal of Group II of the Periodic Table, to produce a polymer containing the divalent metal as part of the polylactide. Either optical isomer of lactide may be used, and the lactide can be copolymerized with other cyclic esters having from 6 to 8 carbon atoms in the ring, such as glycolide or tetramethyl glycolide.

U.S. Pat. No. 4,045,418 to Sinclair discloses thermally stable copolymers of optically inactive lactide and epsilon caprolactone with a tin ester of carboxylic acid serving as a catalyst to produce throwaway thermoplastic objects that are environmentally attractive because they slowly degrade to harmless substances. Cyclic esters such as glycolide, lactide and the lactones are also disclosed as being used to produce thermoplastics. U.S. Pat. No. 4,057,537 also to Sinclair discloses the copolymerization of glycolide with lactide and various lactones to form copolymers which are reported as useful in making absorbable sutures. Sinclair's primary objective is to produce a non-gummy, high impact, non-brittle, thermally stable copolymer of an optically active lactide and epsilon-caprolactone which can be fabricated into various thermoplastic objects that are disposable and environmentally attractive since they degrade into harmless substances.

U.S. Pat. No. 3,844,987 to Clendinning et al, discloses shaped containers fabricated from biodegradable thermoplastic oxyalkanoyl polymers, such as epsilon-caprolactone polymers, and naturally occurring biodegradable substances to serve as containers in which to germinate and grow seed or seedlings.

U.S. Pat. No. 3,636,956 to Schneider discloses copolymers of L(−)lactide with up to 35% glycolide for use in surgical applications such as sutures and ligatures.

U.S. Pat. No. 3,739,773 to Schmitt et al, discloses polyglycolic acid or polyhydroxyacetic ester can be surgically used for a solid prosthesis or a protective gauze and is absorbable by living mammalian tissue.

U.S. Pat. No. 3,736,646 to Schmitt discloses a copolymer containing 15 to 85 mole % of both glycolic and lactic acid can be formed into biodegradable surgical structures such as tubes or sheets or spun as filaments to prepare sutures.

U.S. Pat. No. 4,300,565 to Rosensaft et al, discloses a method for producing sterile surgical articles from a synthetic absorbable copolymer formed by copolymerizing glycolide monomer with a cyclic ester monomer other than a glycolide, such as a lactone, oxalate or carbonate.

U.S. Pat. No. 3,531,561 to Trehu discloses the use of high molecular weight polylactides extruded to form a surgical suture.

U.S. Pat. No. 4,539,981 to Tunc discloses an absorbable bone fixation device made from a polymer of L(−)lactide with an inherent viscosity above 4.5.

U.S. Pat. No. 4,181,983 to Kulkarni discloses an assimilable, porous, hydrophilic prosthesis composed of a polymer of hydroxycarboxylic acid, with the preferred polymer being a lactic acid.

U.S. Pat. No. 4,137,921 to Okuzumi discloses the formation of highly crystalline, fiber-forming addition copolymers of lactide and glycolide having from 50 to 75% glycolide. The lactide-glycolide addition copolymers are highly crystalline and useful in forming fibers for surgical sutures.

U.S. Pat. No. 3,839,927 to Wasserman et al, discloses the formation of a high molecular weight l-lactide/-glycolide copolymer using a stannous octoate catalyst. The copolymer may be extruded to form filaments useable as absorbable sutures.

European Patent Application No. 0204931 to Pertti et al, discloses a synthetic polymeric surgical osteosynthesis material absorbable by the body composed of such polymers as a polylactide.

Other patents of interest relating to the preparation of polylactides include U.S. Pat. Nos. 2,703,316 to Schneider; 2,890,208 to Young et al; 2,362,511 to Teeters; 3,169,945 to Hostettler et al; 3,284,417 to Hostettler et al; 2,758,987 to Salzburg et al and Canadian Patent 779,291 to Kleine.

SUMMARY OF THE INVENTION

The present invention is based upon the discovery of a biodegradable, biocompatible, resorbable infusion stent comprising a terpolymer of:
 (a) L(−)lactide,
 (b) glycolide, and
 (c) epsilon-caprolactone.

This invention is also based upon a method for treating ureteral obstruction or impairment by utilizing a biodegradable, biocompatible, resorbable infusion stent, and a method for controlling the rate of biodegradation of the stent.

DESCRIPTION OF THE PREFERRED EMBODIMENTS

In accordance with the present invention, it has been found that a biocompatible, biodegradable, resorbable infusion stent can be made from a terpolymer of:

(a) L(−)lactide,
(b) glycolide, and
(c) epsilon-caprolactone.

The inventive infusion stent has the following properties:
  (i) a minimum tensile strength of at least about 500 psi, preferably at least about 650 psi,
  (ii) an elongation greater than about 10%, preferably greater than about 100%,
  (iii) Shore A hardness of about 50 to 100, preferably about 75 to 95

In addition, the biodegradable stent is pliable, and can be fabricated or extruded into tubing with an inside diameter that can vary from about 0.050 to about 0.075 inches, and an outside diameter than can vary from about 0.075 to about 0.120 inches.

The inventive stent can be made transparent and is biocompatible. Because it is also biodegradable, the stent disintegrates in mammalian body tissue, within a few weeks to a few months, without interfering with urinary function.

The inventive stent can be fabricated with a pliable curl set at each end by heat setting techniques, can be sterilized, and is capable of being compounded with radiopaque materials such as barium sulfate. The stent should have a minimum curl strength of at least about 4 grams, and a minimum break strength of about 1.7 pounds. The stent can also be imprinted with biocompatible inks.

It has been found that the controlling factor in the stiffness of the terpolymer composition used in making the stent is the amount of epsilon-caprolactone which can vary between about 15 and about 25% by weight of the terpolymer composition. At about 15 weight % or less, the terpolymer composition becomes too stiff, and at about 25 weight % or higher, the composition becomes too pliable and weak to construct the stent. A 20 weight % caprolactone terpolymer is most preferred for its pliability characteristics.

The amounts of L(−)lactide can vary from about 45 to 85 weight %, preferably about 55 to 75 weight % and most preferably about 60 to 70 weight % of the terpolymer composition.

The amounts of glycolide can vary from about 5 to 50 weight %, and preferably about 10 to 30 weight % of the terpolymer composition. The blending of those components produces a pliable, transparent, thermoplastic elastomer that is biodegradable and biocompatible.

The mechanism of biodegradation of the inventive stent is essentially one of hydrolysis; that is, the destruction, decomposition, or alteration of the chemical composition of the stent by water to the point where the stent disintegrates and is harmlessly excreted from the body in the urine. At the same time, certain portions of the stent which are in contact with the body tissues are resorbed into the tissues. For purposes of this invention, the terms "biodegradation, biodegradable" and the like are intended to also include resorption of the stent in the body tissues.

It has been found that when the glass transition temperature ($T_g$) of the biodegradable composition which comprises the stent is less than about 37° C., biodegradation proceeds at a more rapid rate than when the $T_g$ is about 37° C. or greater.

$T_g$ is defined as a second order transition temperature which results in a discontinuity of properties of a polymer composition. At the $T_g$, the polymer will change from a stiff to a more flexible state, and its density and molecular free volume will increase.

Thus, when the $T_g$ is less than about 37° C., the polymeric composition comprising the stent becomes more susceptible to penetration by body fluids and the time of biodegradation proceeds more rapidly.

The process of biodegradation of the stent begins from the time the stent is initially implanted between the kidney and bladder. However, the rate at which biodegradation occurs can be controlled to assure that the stent will function for the desired period of time which can range from a matter of weeks to two or three months or even longer as the requirement demands, based upon the individual condition and needs of the patient. Most preferably, the useful life of the stent, which is the time during which the stent continues to function and operate, will vary from about 3 to 7 weeks.

Factors which are influential in controlling the rate of biodegradation, which directly relate to the useful life of the stent, include the molecular weight of the stent composition and the amorphous nature of the stent composition. A reduction in molecular weight is indicative of biodegradation. The more amorphous the stent terpolymer composition is, the faster it will biodegrade.

The inventive terpolymer should have a weight average molecular weight of about 20,000 to 1,000,000. preferably about 50,000 to 400,000, and is generally monomodal with respect to molecular weight distribution.

The inventive terpolymer can be melt processed without decomposing at temperatures of 230° C. and below. The terpolymer is thixotropic and most readily processable at temperatures from about 135° to 150° C.

Important factors involved in tube fabrication include the shear rate in the extruder and temperature. The preferred processing temperature for tube extrusion varies from about 135° to 150° C. Processing at all conditions reduces the average molecular weight and affects all molecules similarly. The shear rate in the extruder should be maintained as low as possible to reduce the amount of melt fracture and molecular weight degradation. Thus, it is important in the processing to preferably maintain the shear rate in the extruder to about 500 to 1000 sec$^{-1}$ to maintain physical properties as close to the original material as possible.

It is also desirable to incorporate or blend radiopaque materials such as barium sulfate with the terpolymer in amounts varying from about 5 to 30 weight %, preferably about 10 to 20 weight % of the terpolymer composition. The barium sulfate is finely divided to a particle size which makes it homogeneous and compatible with the terpolymer, without affecting its light transmission properties. A suitable particle size is where 99% of the particles pass through 325 mesh or a 45 micron opening.

The present invention also provides a method for treating and remedying a ureteral obstruction or impairment with a ureteral stent without the necessity for an additional surgical procedure to remove the stent after it has performed its function and is no longer needed. The use of the inventive biodegradable, biocompatible and resorbable ureteral stent assures its safe and innocuous disappearance by biodegradation at a controlled and predictable rate after the stent has fulfilled its function. The controlled predictable rate of biodegradation is based upon such factors as molecular weight and extent of the amorphous nature of the terpolymer composition. Thus, the only surgical procedure necessary is the initial insertion and positioning of the ureteral stent between the kidney and the bladder. Removal is accomplished by biodegradation of the stent.

The following examples illustrate specific embodiments of the present invention. In the examples and throughout the invention all parts and percentages are by weight, unless otherwise indicated.

EXAMPLE 1

Starting Materials

High-purity L(−)lactide is available from commercial sources, under the trademark Crystallization 3 TM from Purac Inc., affiliated with CCA biochem bv. of The Netherlands, and under the trademark L-Lactide S TM from Henley and Co., a subsidiary of Boehringer Ingelheim of Germany. Glycolide is available under the trademark Glycolide S TM from Henley and Co.

Epsilon-caprolactone having a purity above 99% is purchased from commerical sources, such as Aldrich Company Catalog No. 16736-3, and is further purified by vacuum distillation through a Claisen head at 10 to 20 torr, to a water white cut at 90° to 115° C. with a boiling point range of about ±2° C. The distillation i discontinued when the pot supply is low and with the temperature rising at constant pressure. The distillate is stored under a moisture free nitrogen or argon atmosphere.

The catalyst, stannous octoate, is available from M&T Chemicals, Rahway, NJ as an anhydrous solution. About 10 milliliters of dried CP (certified pure) or AP (analyzed pure) grade toluene and 20 milliliters of stannous octoate was pipetted into a 200 to 300 ml flask, equipped with either an argon or nitrogen purge and a Dean-Stark type trap that was capped with a Drierite drying tube. The empty apparatus was previously flame-dried and cooled under nitrogen. The toluene solution was brought to reflux under a nitrogen trickle and 10 milliliters was distilled, to insure that the last few milliliters were clear.

EXAMPLE 2

Preparation of Terpolymer 65 parts of L(−)lactide (L-lactide S TM , Henley and Co.), 15 parts of glycolide (Glycolide S TM , Henley and Co.), and 20 parts of purified epsilon-caprolactone, (Aldrich Catalog No. 16736-3; Chemical Abstracts No. 502-44-3) were placed in an ampoule followed by the addition of 0.10 milliliters of a 20% stannous octoate solution in toluene. The amount of stannous octoate catalyst solution was 0.10 milliliters per 100 grams of total lactide, glycolide and epsilon-caprolactone. The ampoule was evacuated with a vacuum pump for at least 10 minutes and sealed at its constriction. The contents were melted by placing the ampoule in a 140° to 160° C. oil bath, while mixing the melt by swirling until the melt became viscous. Heating continued for about 16 to 72 hours at 140° to 160° C. The ampoule was removed from the oil bath, and cooled to room temperature. The terpolymer product was removed from the ampoule and stored in a desiccator. The terpolymer was transparent and nearly colorless. Its weight average molecular weight, as measured by gel permeation chromatography (GPC) was greater than 100,000.

The preparatory procedure was again repeated using different amounts of the components as tabulated in Table 1.

TABLE 1

| TERPOLYMER COMPOSITION, Weight % | | | |
|---|---|---|---|
| Sample No. | L(-)lactide | Glycolide | Epsilon-caprolactone |
| 1 | 60 | 15 | 25 |
| 2 | 37.5 | 37.5 | 25 |
| 3 | 15 | 60 | 25 |
| 4 | 65 | 15 | 20 |
| 5 | 85 | 0 | 15 |

Each of the samples was then tested for various physical properties tabulated in Table 2.

TABLE 2

| SUMMARY OF PHYSICAL PROPERTIES | | | | |
|---|---|---|---|---|
| Sample No. | Tensile[a] Strength, psi | Elongation[a] percent | Modulus[b] | Shore, A |
| 1 | 1627 | 596 | 506 | 51 |
| 2 | 439 | 600 | 377 | 52 |
| 3 | 1383 | 35 | 8791 | 96[c] |
| 3 | 1693[d] | 40 | 9908 | 96 |
| 4 | 1511 | 954 | 4035 | 94 |
| 4[e] | 1654 | 564 | 382 | 60 |
| 5 | 4558 | 275[f] | 110,368 | (Shore D,75) |

Footnotes for Table 2
[a]Average of 5 specimens, ASTM D-638, 70 mil thickness, crosshead speed 20 in./min.
[b]Plastic or initial tangent modulus.
[c]Shore D: 54
[d]Crosshead speed 2 in./min.
[e]Tested at 37° C.
[f]To failure, but 5% to yield.

EXAMPLE 3

Compression Molding of Terpolymers

Sheets of approximately 75 mil were compression molded in accordance with the following procedure:

60 grams of each terpolymer sample prepared in accordance with Example 2 were placed between silicone release paper in a polished, stainless steel hinged mold preheated in a press to the temperatures shown in Table 3.

TABLE 3

| Sample No. | Molding Temp. °F. | Platen Pressure (psi) |
|---|---|---|
| 1 | 250 | 5,000 for 2 min. 10,000 for 3 min. |
| 2 | 250 | same as sample No. 1 |
| 3 | 205 | " |
| 4 | 266 | " |
| 5 | 330 | 20,000 for 1 min. |

Contact pressure was maintained on the mold for approximately 2 to 5 minutes until the polymer flowed into the mold cavity. Platen pressure of 5,000 to 2,000 pounds was applied for 1 to 3 minutes as shown in Table 2. The mold was then put into a cooling press under the same platen pressure and held until cooled to room temperature. The sheet of polymer for each sample was removed from the mold and release paper and specimens were cut from the sheet for tensile tests, with the results tabulated in Table 4.

TABLE 4

| ELASTOMER MODULI AT 100 AND 200% ELONGATION[a] | | |
|---|---|---|
| Sample No. | 100% Modulus (psi) | 200% Modulus (psi) |
| 1 | 155 | 227 |
| 2 | 162 | 188 |
| 3 | 446 | 489 |
| 4 | 214 | 294 |

TABLE 4-continued

ELASTOMER MODULI AT 100 AND 200% ELONGATION[a]

| Sample No. | 100% Modulus (psi) | 200% Modulus (psi) |
|---|---|---|
| 5 | 2130 | 3160 |

[a]Elastomer modulus is psi load at 100% and 200% elongation.

EXAMPLE 4

Characterization of Molecular Weight and Thermal Properties

A molecular weight analysis and thermal characterization of several samples of L(−)lactide/glycolide/epsilon-caprolactone terpolymer with component ratios of 65/15/20 in parts by weight was conducted.

Molecular weight distribution and averages were determined using a Waters Model 150 C ALC/GPC SEC with a Model 820 data station and Maxima software. Operating parameters used to determine the molecular weight are listed in Table 5. Table 6 shows molecular weights calculated for the samples.

Table 5

Operating Parameters for Molecular Weight Analysis

Columns: $10^6 - 10^5 - 10^4 - 10^3$ Å μ Styragel
Solvent: Burdick & Jackson DIG Tetrahydrofuran
Flow Rate: 1 ml/min
Injection Volume: 100 μl
Temperature: 23° C. (RT)
Nominal Concentration: 2 mg/ml
Detector: Refractive Index
Standards: Narrow distribution polystyrene

TABLE 6

Molecular Weights of Terpolymer Samples Before and After Extrusion Into Tubing

| Description | $M_n$, 1000's | $M_w$, 1000's | $M_z$, 1000's | $M_w/M_n$ |
|---|---|---|---|---|
| Before processing - | | | | |
| Sample 1 | 106 | 197 | 342 | 1.88 |
| Sample 2 | 145 | 310 | 591 | 2.14 |
| Beginning of extrusion - | | | | |
| Sample 1 | 86 | 173 | 300 | 2.01 |
| Sample 2 | 104 | 228 | 526 | 2.18 |
| Middle of extrusion - | | | | |
| Sample 1 | 90 | 177 | 303 | 1.97 |
| Sample 2 | 103 | 204 | 364 | 1.98 |
| End of extrusion - | | | | |
| Sample 1 | 85 | 171 | 302 | 2.00 |
| Sample 2 | .97 | 200 | 375 | 2.07 |

The terpolymers were monomodal with respect to molecular weight distribution. Although the polymers showed a decrease in molecular weight upon melt fabrication, the decrease was not significant in terms of loss of physical properties.

Thermal gravimetric analysis (TGA) and differential scanning calorimetry (DSC) were performed on the terpolymers. Inhomogeneity, as evidenced by melting points of monomers, or weight loss on programmed heating, as well as melting points of homopolymers was not detectable. The terpolymers were pure and homogeneous, and contained at most ppm quantities of unreacted monomer. The terpolymer could be melt processed without decomposition at 230° C. and below.

The material was thixotropic (shear thinning) and processible at approximately 138°-148° C.

EXAMPLE 5

Formation of Small Diameter Tubes

A Brabender single screw ¾ inch diameter extruder with 30 L/D was used with a die to manufacture small tube diameters. The take up device, a Univex Take-off from C. W. Brabender, was placed after a 6 foot water bath. The terpolymer composition of Example 4 was used. The initial processing temperatures for tube extrusion were 138° to 148° C. The shear rate in the extruder was maintained in the range of 500 to 1000 sec.$^{-1}$ to minimize the amount of melt fracture and molecular weight degradation. The molecular weights were determined using Maxima 820 GPC analysis, with results shown in Table 7 as follows:

TABLE 7

| Temperature °C. | Molecular Weights | |
|---|---|---|
| | $M_n$ Number Average | $M_w$ Weight Average |
| Unprocessed control | 126412 | 295015 |
| 138 | 103062 | 203780 |
| 148 | 90005 | 176878 |

The extrusion temperature profile from the feed zone to the die was as follows:

| Zone | Temperature °C. |
|---|---|
| 1 (feed) | 138 |
| 2 | 143 |
| 3 | 146 |
| 4 (die) | 148 |

The terpolymer was extruded to produce a tube with an inside diameter of 0.072 inch and outside diameter of 0.111 inch. This test demonstrated that the biodegradable terpolymer can be extruded into small tubes with the desired diameter using the processing conditions described. Important factors involved in tube fabrication were shear history and temperature. Processing at all conditions reduced the molecular weight averages and affected all molecules similarly. Thus, it was important in the processing to maintain the shear rate in the extruder at a minimum to maintain original material properties. The processing temperature also affected the final molecular weight. The higher the processing temperature, the lower the calculated molecular weight averages. Therefore, it is preferable to operate the extruder at the low end of the processing temperature range of the terpolymer (138° to 148° C.).

EXAMPLE 6

Blending of Terpolymer with Barium Sulfate Followed by Extrusion

A terpolymer having the same composition as that in Example 5 was melt blended with 12 percent by weight of small, micron size particulate BaSO$_4$ on a two roll mill at 280° F. The BaSO$_4$ was homogeneous and compatible with the terpolymer. The terpolymer resin filled with the BaSO$_4$ was then ground with dry ice and placed in an oven at 100° F. for 1 hour to remove excess moisture. To complete the drying, the material was placed in a vacuum oven at room temperature overnight.

The filled copolymer was extruded into a tube using a ⅜ inch Brabender extruder with 30:1 length to diameter ratio. Additional die parts were used for the small diameter requirements. A 6-foot water bath and a take up device followed the extruder to cool and control the size of the tubing. Air was also fed through the middle of the die to maintain the tube shape until the material cooled and established its own integrity. The final tube diameter was determined by balancing the extruder rpm, air pressure, and take up speed with the die dimensions. The processing temperatures used in the fabrication of the tubing were:

| Temperature Profile (°F.) | | | |
|---|---|---|---|
| T1 (feed) | T2 | T3 | T4 (die) |
| 290 | 300 | 310 | 320 |

The tubing was able to be heat-set into approximately a 1 inch diameter curl by looping it around or within a mandril, heating the curled tubing to 42°-50° C. (108°—122° F.) and cooling it in place. The curl, thus formed, promptly returned to its position when straightened.

The molecular weight of the BaSO$_4$ filled terpolymer tubing was then determined. The weight average-, number average-, and Z-average molecular weights, respectively, were 260,000; 152,000; and 442,000. This demonstrated that the terpolymers can be processed to retain useful properties for applications as a stent. The tubing extrudates were of good quality - smooth, homogeneous, tough, and elastic. Preliminary results indicated that the tubing embrittled somewhat after 3 weeks in contact with aqueous fluids. Although it was still somewhat pliable, ductile failure occurred upon handling and bending. At that stage, the $M_w$, $M_n$, and $M_z$, respectively, were 27,600; 10,400; and 51,623. The polydispersity ($M_w/M_n$) was 2.65, which is a slight increase over the value of 2.0 for the unexposed terpolymer (see Table 7).

Differential scanning calorimetry indicated substantial hydrolysis and degradation. After 6-7 weeks the walls of the tubing appeared much thinner. The terpolymer tubing became softer and somewhat fibrous, and shredded easily into soft pieces.

Although the composition comprising the inventive biodegradable, biocompatible, resorbable ureteral stent has been disclosed in the context of a terpolymer of L(—)lactide, glycolide and epsilon-caprolactone, other equivalent compositions are also contemplated as being suitable compositions for preparing the stent.

Thus, it is contemplated that D(—)lactide, the internally optically inactive meso-lactide and the optically inactive racemic or D,L-lactide can be substituted for the L(—)lactide. It is also contemplated that delta-vacero-lactone can be substituted for epilson-caprolactone.

A discussion of the mechanism of biodegradation of these compounds in the form if films is disclosed in Pitt et al "Alphatic Polyesters II. The Degradation of Poly (DL-Lactide), Poly (Epilson-Caprolactone), and Their Co-Polymers In Vivo", BIOMATERIALS, pages 215-220, (Vol. II, October 1981).

What is claimed is:

1. A biodegradable, biocompatible, resorbable, ureteral stent having retaining means to prevent migration from a predetermined position in the ureter, said stent comprising a terpolymer of:
   (a) L(—) lactide
   (b) glycolide, and
   (c) epsilon-caprolactone.

2. The ureteral stent of claim 1, wherein the epsilon-caprolactone varies from about 15 to 25 weight %.

3. The ureteral stent of claim 1, wherein the L(—)lactide varies from about 45 to 85 weight %.

4. The ureteral stent of claim 1, wherein the glycolide varies from about 5 to 50 weight %.

5. The ureteral stent of claim 1, also including about 5 to 30 weight % of a radiopaque material.

6. The ureteral stent of claim 5, wherein said radiopaque material is finely divided barium sulfate.

7. The ureteral stent of claim 1, wherein the modulus varies from about 6000 to 7000 psi.

8. The ureteral stent of claim 1, bendable into a pliable curl set at each end.

9. The ureteral stent of claim 1, sterilizable and capable of compounding with radiopaque materials.

10. The ureteral stent of claim 1, in transparent form.

11. The ureteral stent of claim 1, wherein the terpolymer has a weight average molecular weight varying from about 20,000 to 1,000,000.

12. The ureteral stent of claim 1, wherein the terpolymer has a melt process decomposition temperature greater than or equal to about 230° C.

13. The ureteral stent of claim 1, wherein the terpolymer has a tube extrusion processing temperature that varies from about 135° to 150° C.

14. The ureteral stent of claim 11, wherein, the terpolymer has a weight average molecular weight of about 50,000 to 400,000.

15. The ureteral stent of claim 1, having:
   (i) a tensile strength of at least about 500 psi,
   (ii) an elongation greater than about 10%, and
   (iii) Shore A hardness of about 50 to 100.

16. A method for treating ureteral obstruction or impairment in a mammalian host by inserting in the ureter in a predetermined location, a biodegradable, biocompatible resorbable non-anastomosis polymeris stent extending between the kidney and the bladder, said stent having end portions with pliable retaining means to prevent migration before biodegradation, without the need for suturing, from the predetermined location in the ureter.

17. The method of claim 16, wherein said stent has the following properties:
   (i) a tensile strength of at least about 500 psi,
   (ii) an elongation greater than about 10%, and
   (iii) Shore A hardness of about 50 to 100.

18. The method of claim 16, wherein the stent has the following properties:
   (a) tensile strength greater than 1000 psi,
   (b) elongation greater than 100%, and
   (c) Shore A hardness of about 75 to 95.

19. The method of claim 16, wherein said stent comprises a polymeric material having a weight average molecular weight varying from about 50,000 to 400,000.

20. The method of claim 16, wherein the stent comprises at least one polymer selected from the group consisting of L(—)lactide, glycolide, epsilon-caprolactone, D(—)lactide, meso-lactide, D,L-lactide, and delta-valero-lactone.

21. The method of claim 29, wherein the stent comprises of terpolymer of:
   (a) L(—)lactide, (b) glycolide, and (c) epsilon-caprolactone.

22. The method of claim 21, wherein the L(—)lactide varies from about 45 to 85 weight %.

23. The method of claim 21, wherein the glycolide varies from about 5 to 50 weight %.

24. The method of claim 21, wherein the epsilon-caprolactone varies from about 15 to 25 weight %.

25. A method for controlling the time of biodegradation in the ureter of a polymeric, biodegradable, biocompatible, resorbable non-anastomosis ureteral stent by (a) inserting a stent in the ureter in a predetermined location between the kidney and the bladder to relieve ureteral obstruction;

(b) providing end portions of the stent with pliable retaining means to prevent migration of the stent before biodegradation, without the need for suturing; and (c) controlling the rate of biodegradation of said polymeric stent from a few weeks to a few months, by varying the molecular weight of the polymer composition comprising the stent, from a weight average molecular weight of about 20,000 to about 1,000,000.

26. The method of claim 25, wherein the stent comprises a terpolymer of:

(a) L(—)lactide, (b) glycolide, and (c) epsilon-caprolactone.

27. The method of claim 25, wherein the weight average molecular weight of said polymeric stent varies from about 50,000 to about 400,000.

28. The method of claim 25, wherein the stent comprises at least one polymer selected from the group consisting of L(—)lactide, glycolide, epsilon-caprolactone, D(—)lactide, meso-lactide, D,L-lactide, and delta-valero-lactone.

29. The method of claim 25, wherein the average molecular weight varies from about 50,000 to about 400,000.

30. The method of claim 25, wherein said stent has the following properties:

(i) a tensile strength of at least about 500 psi, (ii) an elongation greater than about 10%, and (iii) Shore A hardness of about 50 to 100.

31. A method for relieving ureteral obstruction in a mammalian host, comprising:

(a) forming a tubular polymeric, biodegradable, biocompatible resorbable non-anastomosis ureteral stent having end portions with pliable retaining means to prevent migration before biodegradation, without the need for suturing, from a predetermined position in the ureter, and wherein said stent substantially extends from the kidney to the bladder;

(b) controlling the rate of biodegradation of said polymeric stent by varying the molecular weight of the polymer composition comprising the stent, from a weight average molecular weight of about 50,000 to about 1,000,000, and (c) inserting said positioning said ureteral stent in the ureter in a predetermined location between the kidney and the bladder.

32. The method of claim 31, wherein said stent has the following properties:

(i) a tensile strength of at least about 500 psi, (ii) an elongation greater than about 10%, and (iii) Shore A hardness of about 50 to 100.

* * * * *

UNITED STATES PATENT AND TRADEMARK OFFICE
CERTIFICATE OF CORRECTION

PATENT NO. : 5,085,629

DATED : February 4, 1992

INVENTOR(S) : Goldberg et al

It is certified that error appears in the above-identified patent and that said Letters Patent is hereby corrected as shown below:

At column 9, line 58, change "vacero-lactone" to

--valerolactone--.

At column 10, line 42, change "polymeris" to --polymeric--

Signed and Sealed this

Sixth Day of July, 1993

Attest:

MICHAEL K. KIRK

Attesting Officer     Acting Commissioner of Patents and Trademarks